United States Patent [19]

Eichenlaub

[11] 4,411,265
[45] Oct. 25, 1983

[54] EAR WAX REMOVING DEVICE

[76] Inventor: John E. Eichenlaub, 1300 France Ave. South, Golden Valley, Minn. 55416

[21] Appl. No.: 275,209

[22] Filed: Jun. 19, 1981

Related U.S. Application Data

[63] Continuation of Ser. No. 49,179, Jun. 18, 1979, abandoned.

[51] Int. Cl.³ .............................................. A61F 7/12
[52] U.S. Cl. .................................. 128/303.1; 128/304; 128/400; 128/401
[58] Field of Search ................. 128/304, 303 R, 305, 128/303.1, 303.11, 303.12, 348, 399–401, 24 A, 24.1, 24.2, 32, 34, 35, 255; 30/140; 15/105, 110

[56] References Cited

U.S. PATENT DOCUMENTS

| | | | |
|---|---|---|---|
| 2,077,453 | 4/1937 | Albright | 128/401 |
| 2,617,420 | 11/1952 | Jozefczyk | 128/304 |
| 3,099,263 | 7/1963 | Palazzolo | 128/304 X |
| 3,425,419 | 2/1969 | Dato | 128/303.1 |
| 3,956,826 | 5/1976 | Perdeaux | 128/24 A X |
| 4,106,496 | 8/1978 | Proctor et al. | 128/401 X |

FOREIGN PATENT DOCUMENTS 527365 7/1956 Canada ............................. 128/329 R
362997 11/1922 Fed. Rep. of Germany ...... 128/304

OTHER PUBLICATIONS

Variations of a thumb forcep, such as the Taylor device "I".
Various alligator style forceps, such as the Hartman, "II".
Ear spoons, such as the Gross, "III", also shown in the otology instrument advertising submitted herewith.
Ear curettes, such as the one identified as Billeau, "IV" and Buck V.
Ear syringes such as the one identified "VI" in the advertising literature submitted herewith.

Primary Examiner—Michael H. Thaler
Attorney, Agent, or Firm—Schroeder, Siegfried, Vidas & Arrett

[57] ABSTRACT

An ear wax removing device comprised of a hollow curette connected to a source of circulating warm fluid and movably mounted in forwardly and gently biased relation for longitudinal movement upon a mounting plate which is designed to rest against the side of the patient's head and carries an adjustable abutment which limits the depth of insertion of the curette into the patient's ear.

12 Claims, 3 Drawing Figures

EAR WAX REMOVING DEVICE

This is a continuation of application Ser. No. 049,179, filed June 18, 1979, now abandoned.

The formation of wax takes place in the ears of all humans and normally presents no serious problem because it works out as a result of a milking action imparted to the ear canal by the motion of the individuals' jaws. Wax does accumulate, however, in the ears of relatively few people and sometimes does present a serious problem unless properly removed. Such accumulation may result from a tortuous ear canal, an abnormal rigidity of the ear canal cartilages, or less than adequate chewing processes by the patient because of a preference for soft foods.

The accumulation of an undue amount of wax may, as is most commonly the case, impair the hearing of the patient. Other undesirable and sometimes painful consequences of such an undue accumulation of ear wax may include pain, and itching or discharge, or even indigestion which may result from vagal nerve reflex.

Heretofore, the traditional remedy provided such serious accumulation of wax in the ear has been to flush the wax out with warm water having a temperature considerably above the body temperature, but not hot enough to burn the tender canal passages. This traditional method has a number of serious disadvantages, however. For example, if the patient has suffered a perforated ear drum (which cannot be seen because the accumulated wax blocks that condition from view), the warm water may pick up bacteria from the germ-laden ear canal and convey the same into the middle ear and mastoid areas. Such areas are normally sterile and can easily become infected. Also, if the syringe by means of which the warm water is introduced into the ear has a tip of sufficiently large size to occlude the ear outlet, pressure may be built up and the eardrum ruptured thereby. In addition, hot water sometimes stimulates the labyrinthine nerves and thereby causes dizziness or nausea, or both. Moreover, such ear-flushing operations are time consuming and messy.

It is a general object of my invention to provide a novel and improved means for removing wax accumulations from the human ear.

A more specific object is to provide a novel and inexpensive device for more effectively and safely removing wax accumulations from the human ear.

A still more specific object is to provide novel means for removing wax accumulations from the human ear which is easy and simple to utilize, is inexpensive to produce, and avoids the introduction of fluid into the ear and hence, the disadvantages hereinbefore outlined.

Another object is to provide novel means for removing wax accumulations from the human ear, which is more simple, safer, and requires less time than those heretofore known.

These and other objects and advantages of the invention will more fully appear from the following description, made in connection with the accompanying drawings, wherein like reference characters refer to the same or similar parts throughout the several views, and in which.

Figure 1:
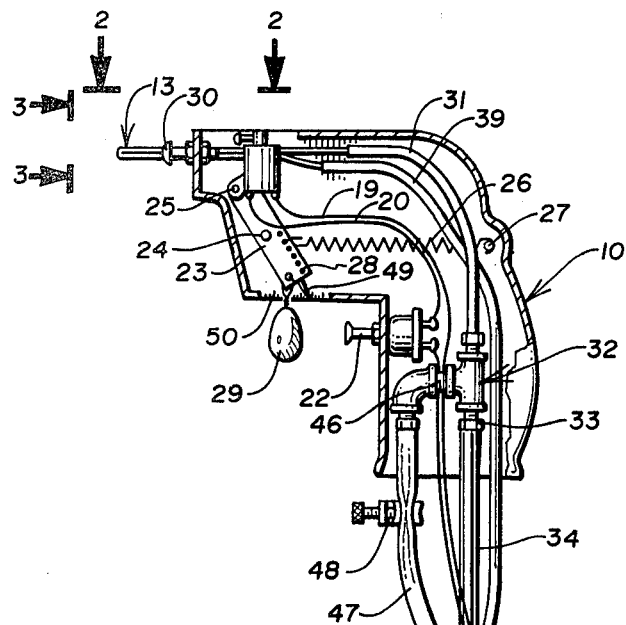
FIG. 1 is a side elevational view of the preferred form of my ear wax removing device with portions thereof shown in vertical section.
Figure 2:
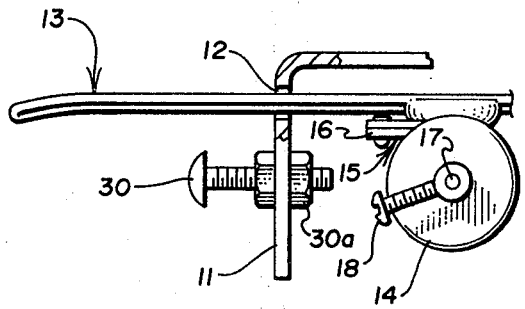
FIG. 2 is a top plan view of an enlarged scale of the forward end of my ear wax removing device, taken along line 2—2 of FIG. 1.
Figure 3:
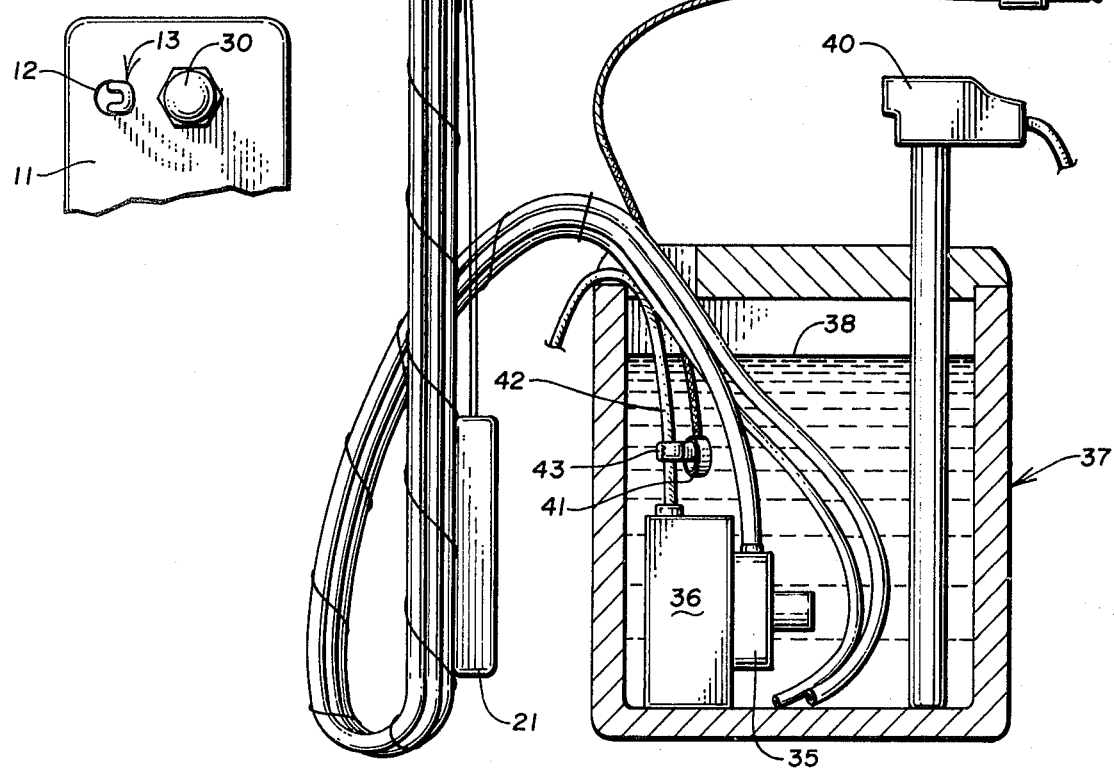
FIG. 3 is a fragmentary end elevational view taken on an enlarged scale of the front end of my ear wax removing device along line 3—3 of FIG. 1.

The preferred embodiment of my invention, as shown in FIGS. 1-3, includes a mounting plate 10 which, as shown, is pistol shaped and has a forward end portion 11 extending at right angles to its general plane. An opening 12 in this forward end portion accommodates and slidably mounts a curette 13 which is tubular in form and may be formed of any suitable material such as, for example, a 15 gauge hypodermic needle tubing. Fixedly mounted on the rear end portion of the curette 13 is a vibrator 14 which may, as shown, be in the form of a small electric motor having a mounting bracket 15 secured to one side thereof with an ear 16 extending outwardly therefrom for a purpose to be hereinafter described. The motor 14 has a drive shaft 17 extending outwardly therefrom and to which is secured an off-center weight such as a simple screw 18 which causes the motor 14 and curette 13 to vibrate whenever the motor is driven. Electric lines 19 and 20 extend from the motor 14 to a source of electric motor 21 as shown in FIG. 1. A normally open switch 22 is interposed within the line 20 so that the motor may be operated at will by the physician performing the ear wax removing operation by simply pressing the forwardly extending switch element shown in that Figure. A lever member 23 is pivotally mounted on the plate 10 at its fulcrum 24 and is pivotally connected by pin 25 to the ear 16 of the mounting bracket 15 so as to support the motor 14 and move the curette 13 forwardly and rearwardly within the opening 12 as will be hereinafter described. A very weak spring 26 is connected by an anchor 27 at one of its ends to the plate 10 and at its other end to the lever 23 at one of a plurality of openings 28 carried by the shorter lever arm of the lever. A counterweight 29 is connected to the lower end of the lever to counterbalance the weight of the motor 14 so that the curette will be actuated only by spring tension rather than being urged forward or back by the weight of the motor.

Carried by the forward portion 11 of the plate 10 is an abutment member 30 which is threadedly received within an internally threaded nut 30a by means of which the extent to which the abutment member extends forwardly of the portion 11 may be readily adjusted.

As indicated previously, the curette 13 is hollow in order to permit fluid to be pumped therethrough. It is reversed upon itself at its forward end and one of its rearward ends is connected to a flexible conduit 31. The opposite end of the conduit 31 is connected to one opening of a T connection 32. The opposite opening of the T connection 32 is connected as at 33 to a flexible conduit 34 which in turn is connected to a submersible circulating pump 35 which is driven by an electric motor 36 located within a tank member 37 that is at least partially filled with a fluid such as water 38. The T connection 32 is fixedly mounted upon the mounting plate so that the latter will support the same and the conduit 34 will move therewith.

The other end of the curette 13 is connected to a flexible return conduit 39 which, as shown in FIG. 1, terminates within the tank 37. A heating unit 40 is also located within the tank 37 to maintain the temperature of the water within a preferred range of 125°–130°

Fahrenheit, which temperature is safe for use upon sensitive tissues such as is found within the ear. The heating unit 40 is adjustable and may be of any of the conventional types utilized in maintaining the temperature of water within a desired range within an aquarium.

A sensor member 41 is supported within the water 38 upon the electric cord 42 of the motor 36 by means of a clamp 43. A cord 44 leads from the sensor unit 41 to a plug 45 which is adapted to be utilized in conjunction with a readout device (not shown) by means of which the temperature of the liquid 38 may be monitored.

Connected to the T 46 of the T connection 32 is a main return conduit 47 through which the warmed fluid 38 will normally return to the interior of the tank 37 except when a clamp member such as clamp 48 is applied thereto. Thus the pump 35 may be operated by the motor 36 continuously to circulate the warm fluid upwardly through the conduit 34, through the T connection 32 into the conduit 47 and return to the interior of the tank when the wax removing device is not in use. When it is desired to utilize the device, the fluid may be forced through the curette 13 by applying the adjustable clamp 48 so as to restrict the flow through the conduit 47 or cut it off entirely if so desired. When this is done, the curette will be quickly warmed to the temperature of the fluid 38 and will be maintained at that temperature while in use.

When the physician desires to utilize my ear wax removing device for the purpose of removing accumulated wax within a patient's ear, he merely applies the clamp 48 or tightens it so as to restrict the flow therethrough sufficiently so as to cause the warm fluid to pass through the curette 13. The heat-conducting material from which the curette 13 is made will cause that element to quickly arrive at the temperature of a fluid passing therethrough and since this temperature is considerably warmer than the body temperature, it will, when applied, facilitate the passage of the curette 13 through or around the mass of accumulated wax in the ear. As the curette is applied to the ear, it will engage the accumulated wax, and if the wax has become hard and/or relatively dry, it may offer sufficient resistance to the penetrating activity of the curette as to cause the curette to move rearwardly through the opening 12 of the portion 11 of the mounting plate. Such rearward movement of the curette causes the lever member 23 to pivot about its fulcrum 24 and thereby extend the very weak spring 26 slightly. The spring is of a type to provide about a one ounce pressure through the curette 13 against the mass of accumulated wax. By pressing the switch 22 at the same time, the vibrator 14 will commence operation and its vibrations will be transmitted to the curette 13. This vibrating action substantially facilitates the penetration of the mass of wax by the heated curette 13 with the result that the physician will find that he may readily withdraw all or at least portions of the accumulated mass of wax within the ear.

The abutment member 30 extends into the ear and bears against the portions thereof which define the concha opening of the ear. It is impossible for the physician to mistakenly or by accident damage the ear drum since the length of the curette is such that the ear drum will not be engaged thereby when the abutment member 30 is properly adjusted and bears against such concha-defining portions of the ear.

It will be readily seen that by moving the point of attachment of the spring 26 to different openings 28, the amount of pressure applied through the curette 13 may be readily modified since movement of the spring to an opening located below that shown being utilized in FIG. 1 will increase the lever arm to which the spring is attached and consequently increase the pressure applied through the curette 13.

It will also be seen that the extent of rearward movement of the curette relative to the mounting member 10 can be observed by the extent of movement of the indicator 49 relative to the scale 50.

I have found that with a device as is shown herein there is a substantial increase in safety and ease with which the wax may be removed from a patient's ear and that the operation may be accomplished at a very substantial saving in time and effort. Morever, the danger of possible infection normally attendant the heretofore utilized conventional method of flushing the ear with water has been eliminated and the operation is substantially less messy and more convenient. There is substantially less danger of infection because no free fluid is utilized within the ear and there is no danger of damage to the ear drum because the pivotal mounting of the lever which supports the vibrator ensures that no more than a minimum amount of pressure can be applied to the curette 13. Moreover, the right angled portion 11 of the bracket functions as a rest against the face of the patient to further ensure against undue extension of the curette into the recesses of the ear and of consequent injury thereto.

It will, of course, be understood that various changes made be made in the form, details, arrangement and proportions of the parts without departing from the scope of the invention which consists of the matter shown and described herein and set forth in the appended claims.

I claim:

1. An ear wax removing device comprising:
   (a) a mounting member;
   (b) a rigid heated ear wax-softening curette movably mounted on said mounting member for forward and rearward longitudinal movement relative thereto and having a forward end portion and rearward end portion;
   (c) temperature-controlling mechanism connected to said curette in temperature-controlling relation for maintaining the same at above-body temperature;
   (d) a readily yieldable pressure-applying mechanism mounted on said mounting member separate from said curette and connected to said curette for gently urging said curette forwardly relative to said mounting member; and
   (e) a vibrator connected to said curette in vibration-transmitting relation for vibrating the same while it is being moved into the ear.

2. The structure defined in claim 1, wherein said temperature-controlling mechanism connected to said curette includes warm fluid circulating mechanism.

3. The structure defined in claim 1 wherein said temperature-controlling mechanism includes a conduit running through said curette, and warm fluid circulating means connected to said conduit in fluid circulating relation for passing warm fluid through said curette and effectively warming the same.

4. The structure defined in claim 1, wherein said temperature-controlling mechanism includes conduit means running through said curette in heat-transmitting relation for the movement of a warm fluid therethrough to effectively warm the curette to facilitate its penetration into the wax within the ear.

5. An ear wax removing device comprising:
(a) a mounting member;
(b) a curette movably mounted on said mounting member for forward and rearward longitudinal movement relative thereto and having a forward end portion and rearward end portion;
(c) temperature-controlling mechanism connected to said curette in temperature-controlling relation for maintaining the same at above body temperature;
(d) a pressure applying mechanism mounted on said mounting member and interposed between said mounting member and said curette for urging said curette gently forwardly; and
(e) said pressure applying mechanism including a biased lever pivotally mounted on said mounting member and connected with said curette and yieldably and gently urging said curette forwardly.

6. The structure defined in claim 5, wherein said pressure applying mechanism includes:
(f) a lever pivotally mounted on said mounting member at a point between the ends of said lever and having one lever arm connected to said curette; and
(g) resilient means carried by said mounting member and connected to the other lever arm of said lever and yieldably urging said curette forwardly relative to said mounting member and the inner ear, as said curette is inserted into the ear.

7. An ear wax removing device comprising:
(a) a rigid ear wax-softening curette having a forward end portion and a rearward end portion;
(b) temperature control means connected to said curette in temperature-controlling relation;
(c) shiftable resiliently biased mounting mechanism separate from and connected to said curette in supporting relation and yieldably urging said curette forwardly; and
(d) said mounting mechanism including a biased lever pivotally connected to said curette and urging the same forwardly.

8. The structure defined in claim 7,
(e) an indicating scale carried by said mounting mechanism opposite said lever; and
(f) an indicator carried by said lever in juxtaposed position to said scale for indicating on said scale the extent of insertion of said curette into the ear of the patient.

9. An ear wax removing device comprising:
(a) a mounting member;
(b) a curette having a hollow interior and rigid exterior surfaces movably mounted on said mounting member for forward and rearward longitudinal movement relative thereto and having a forward end portion and rearward end portion;
(c) said curette having fluid passages defined within the hollow interior through which a warm fluid may be circulated;
(d) a mechanism connected to said curette for controllably circulating warm fluid therethrough;
(e) curette mounting means movably supporting said curette; and
(f) pressure applying mechanism carried by said means and connected to said curette in pressure-transmitting relation for continuously but gently urging said curette forwardly.

10. An ear wax removing device comprising:
(a) a mounting member;
(b) a curette having a hollow interior and rigid exterior surfaces movably mounted on said mounting member for forward and rearward longitudinal movement relative thereto and having a forward end portion and rearward end portion;
(c) said curette having fluid passages defined within the hollow interior through which a warm fluid may be circulated;
(d) a mechanism connected to said curette for controllably circulating warm fluid therethrough; and
(e) resiliently biased mounting mechanism connected to said curette and supporting and gently urging said curette forwardly.

11. An ear wax removing device comprising:
(a) a mounting member;
(b) a curette having a hollow interior and rigid exterior surfaces movably mounted on said mounting member for free forward and rearward longitudinal movement relative thereto between limits and having a forward end portion and rearward end portion;
(c) said curette having non-elastic fluid passages defined within the hollow interior through which a warm fluid may be circulated;
(d) a mechanism connected to said curette for controllably circulating warm fluid therethrough; and
(e) a vibrator connected to said curette in vibration-transmitting relation.

12. The structure defined in claim 11, and
(f) curette mounting means movably supporting said curette; and
(g) pressure applying mechanism carried by said means and connected to said curette in pressure-transmitting relation for urging said curette gently forwardly while the latter is vibrated by said vibrator.

* * * * *